US008641856B2

(12) United States Patent
Krattiger

(10) Patent No.: US 8,641,856 B2
(45) Date of Patent: Feb. 4, 2014

(54) METHOD AND SOLDER FOR FORM-FITTED JOINING OF TWO SURFACES

(75) Inventor: Beat Krattiger, Beringen (CH)

(73) Assignee: Storz Endoskop Produktions GmbH (DE)

( * ) Notice: Subject to any disclaimer, the term of this patent is extended or adjusted under 35 U.S.C. 154(b) by 316 days.

(21) Appl. No.: 12/827,581

(22) Filed: Jun. 30, 2010

(65) Prior Publication Data

US 2011/0100545 A1 May 5, 2011

(30) Foreign Application Priority Data

Jun. 30, 2009 (DE) .......................... 10 2009 031 261

(51) Int. Cl.
B29C 65/14 (2006.01)
(52) U.S. Cl.
USPC ...................................... 156/272.2
(58) Field of Classification Search
USPC ........................................... 156/272.2, 272.8
See application file for complete search history.

(56) References Cited

U.S. PATENT DOCUMENTS

| 3,742,181 | A | 6/1973 | Costello |
| 6,239,190 | B1 * | 5/2001 | Wilkinson et al. ............... 522/87 |
| 2003/0015284 | A1 * | 1/2003 | Merdan et al. ............ 156/272.2 |
| 2007/0260325 | A1 | 11/2007 | Wenz |

FOREIGN PATENT DOCUMENTS

| EP | 0160752 A1 | 11/1985 |
| EP | 0076681 B1 | 3/1986 |
| EP | 0251257 A2 | 1/1988 |
| EP | 1693142 A1 | 8/2006 |
| WO | 9622797 A1 | 8/1996 |
| WO | 0130410 A1 | 5/2001 |
| WO | WO 0130410 A1 * | 5/2001 |

OTHER PUBLICATIONS

European Search Report; Application No. EP 10 00 6051; Aug. 13, 2010; 5 pages.
EPO Office Action Application No. 10 006 051.6-2305 Mailing Date: Dec. 16, 2011 4 pages.
EPO Office Action Application No. 10 006 051.6-1652 Mailing Date: Mar. 20, 2013 4 pages.
EPO Office Action Application No. 10 006 051.6-2305 Mailing Date: Aug. 16, 2012 6 pages.
Park J W et al: "Joint structure in high brightness light emitting diode (HB LED) packages" Materials Science and Engingeering A: Structural Materials:Properties; Microstructure & Processing; Lausanne; CH; Bd. 441, Nr. 1-2, Dec. 15, 2006, pp. 357-361, XP027953391, ISSN:0921-5093.

* cited by examiner

Primary Examiner — Daniel McNally
(74) Attorney, Agent, or Firm — St. Onge Steward Johnston & Reens LLC

(57) ABSTRACT

A method for adhesive bond joining of two surfaces, where a metallic or non-metallic solder is applied to at least one of the two surfaces, where the solder has a temperature-dependent optical property. The solder is radiated with electromagnetic radiation with a predetermined spectrum, such that the solder reaches a predetermined temperature above its melting temperature and moistens the surfaces, such that the temperature-dependent optical property is modified reversibly or irreversibly at the predetermined temperature of the solder. The solder is cooled to below its melting temperature, such that the solder solidifies and connects the surfaces in an adhesive bond.

11 Claims, 3 Drawing Sheets

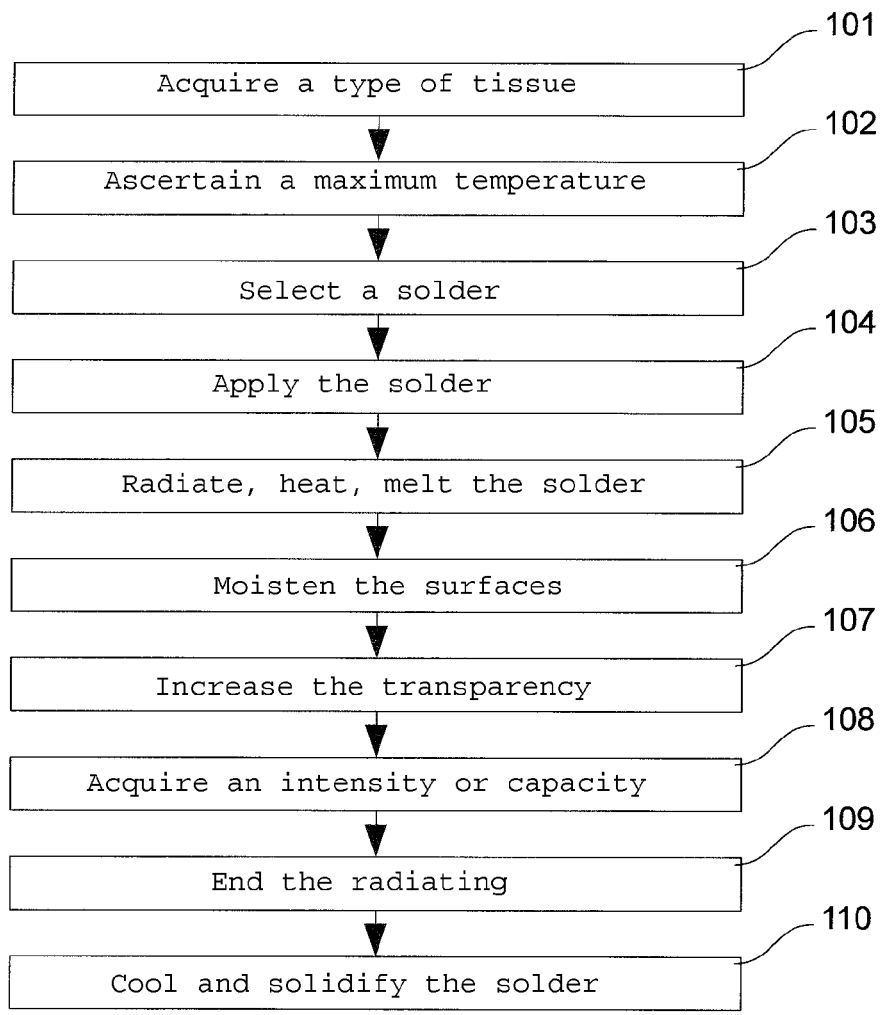
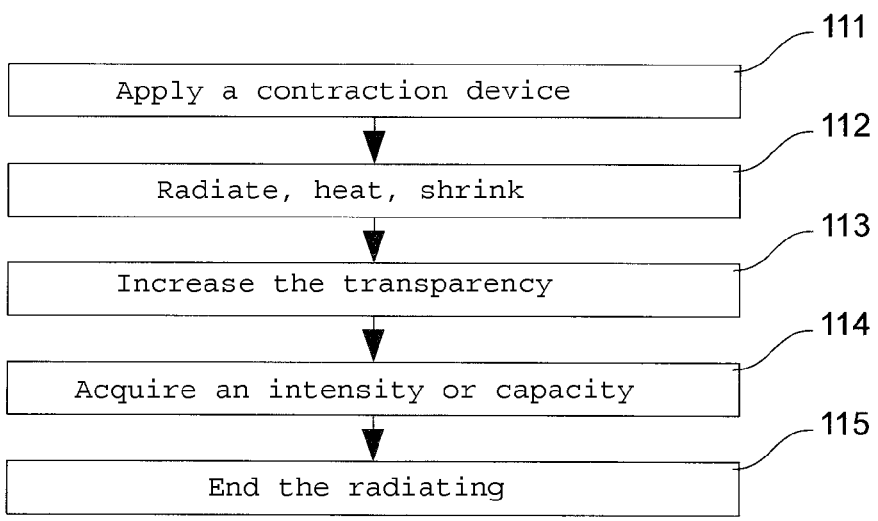

METHOD AND SOLDER FOR FORM-FITTED JOINING OF TWO SURFACES

CROSS-REFERENCE TO RELATED APPLICATIONS

The present application claims priority of German patent application No. 10 2009 031 261.7 filed on Jun. 30, 2009.

FIELD OF THE INVENTION

The present invention relates to a method and a solder for adhesive bond joining of two surfaces, in particular on or in a human or animal body.

BACKGROUND OF THE INVENTION

In endoscopic and conventional medical procedures, surfaces must be joined or durably mechanically connected. For example, openings are closed, or vessels, tendons, or nerves are bound to one another. For some time sutures were exclusively produced by needle and thread for this purpose. Modern processes include tissue welding and tissue soldering.

To solder tissue, for instance, a synthetic material that is degradable in the body (also referred to as a biopolymer) is used as a solder. The solder has a melting temperature that lies above the body temperature in a temperature range at which tissue damage is only temporary or avoided altogether. To heat the solder, infrared radiation is used that is absorbed by the tissue only in small quantities and therefore heats the tissue only to a small degree. The infrared radiation absorbed in the solder heats the solder. The solder melts, moistens the surfaces that are to be joined or mechanically connected, and connects them in a mechanically durable manner after cooling below the melting temperature and congealing, at least until the formation of mechanically load-bearing scar tissue.

Similarly to other soldering methods, the soldering temperature must be controlled precisely. The temperature of the solder and the temperature of the surfaces to be moistened must exceed the melting temperature of the solder, so that the solder completely moistens the surfaces that are to be moistened. The temperature of the bordering tissue may not be so high that the tissue is permanently damaged, or in particular becomes inflamed or dies off.

Unlike with soldering of electrical or electronic components, for instance, the remaining temperature range is relatively small. In addition, the absorbed infrared capacity and the achieved temperature depend on several parameters that are difficult to acquire or control and can vary strongly. These include water or moisture content of the tissue; the distance of the infrared source and the infrared intensity at the site of juncture, especially with endoscopic applications; and the thickness of the solder, which essentially conducts heat more poorly than does metallic solder used in electricity and electronics. In addition, the melting of the solder is often very difficult to recognize optically. It is therefore desirable to have an improved control or regulation of temperatures while soldering.

One object of the present invention is to provide an improved method for adhesive bond joining of two surfaces, an improved solder, a control device for controlling a adhesive bond joining of two surfaces, and a device for adhesive bond joining of two surfaces.

SUMMARY OF THE INVENTION

This object is achieved, in one respect by a method for adhesive bond joining of two surfaces with the following steps: apply a metallic or non-metallic solder to at least one of the two surfaces, such that the solder has a temperature-dependent optical property; radiate the solder with electromagnetic radiation with a predetermined spectrum, such that the solder reaches a predetermined temperature above its melting temperature and moistens the surfaces, such that the temperature-dependent optical property is reversibly or irreversibly modified at the predetermined temperature of the solder, such that the absorption constant decreases upon heating the solder; cool the solder below its melting temperature, such that the solder solidifies and connects the surfaces in adhesive bond manner In another respect, the above object is achieved through a solder for adhesive bond joining of two surfaces by moistening both surfaces by the molten solder and connecting the surfaces by the solidified solder, with a reversibly or irreversibly temperature-dependent optical property.

In yet another respect, the above objects are achieved through a control device for controlling a adhesive bond joining of two surfaces and an apparatus for adhesive bond joining of two surfaces in or on a human or animal body with a control; a light source for radiating the solder with electromagnetic radiation with the predetermined spectrum.

Refinements are indicated in the subsidiary claims.

A few embodiments of the present invention are based on the idea, for adhesive bond joining of two surfaces, of using a non-metallic or even a metallic solder that comprises a reversibly or irreversibly temperature-dependent optical property, in particular a temperature-dependent absorption degree for electromagnetic radiation used to heat the solder. In particular, the absorption degree declines sharply with increasing temperature at a predetermined temperature at or above the melting temperature of the solder. For instance, the absorption degree inside a small temperature interval of 1K, 2K or 5K declines clearly, for instance to two-thirds, one-half, a third, a fifth, or a tenth of the value it has at a temperature below the temperature interval. Therefore the absorbed capacity also declines correspondingly on reaching the predetermined temperature. The result is a slowed rise in temperature of the solder. Depending on the intensity of the heat radiation, on the temperature of the adjacent tissue, and on the heat loss by heat conduction, convection of fluids, and heat radiation, the temperature rise above the predetermined temperature can be strongly slowed or reduced to zero. With an irreversible reduction of the absorption degree, despite non-diminished intensity of the heat radiation the temperature can even decline.

The present invention provides a passive, automatic, or intrinsic regulation of the temperature of the solder. If the predetermined temperature lies in a temperature range in which tissue is not damaged or not damaged beyond a predetermined amount, then under certain conditions it can be ensured that neighboring tissue is not damaged during the soldering process. In addition, the invention can make possible a more uniform heating of the solder even at clearly varying intensity of the heat radiation inside the solder, because areas of the solder that have already been heated to the predetermined temperature absorb less heat capacity. The present invention is also applicable outside of medicine, however, for instance in soldering synthetics or glass.

In a method for adhesive bond joining of two surfaces, a solder, in particular a non-metallic solder, having a temperature-dependent optical property, is applied to at least one of the two surfaces. Before or after it is applied, the solder is radiated with electromagnetic radiation with a predetermined spectral range. In the process, the solder reaches a predetermined temperature above its melting temperature, melts, and moistens both of the surfaces that are to be joined. In addition, the temperature-dependent optical property of the solder is modified reversibly or irreversibly at the predetermined temperature. Upon cooling of the solder below its melting temperature, the solder hardens and provides a adhesive bond connection of the surfaces that are to be joined. The surfaces that are to be joined are, in particular, surfaces of parts of a human or animal body and/or of transplants, implants, or other device s that are to be joined to a human or animal body.

In a method for contracting a contraction device, the contraction device is applied to a surface, in particular a tissue surface, and the contraction device is radiated with electromagnetic radiation with a predetermined spectrum. In the process the contraction device reaches a predetermined temperature and contracts in at least one direction or modifies itself geometrically in some other manner. At the predetermined temperature a temperature-dependent optical property of the contraction device is modified reversibly or irreversibly.

This method can be combined, in particular, with one of the aforementioned methods for adhesive bond joining of two surfaces, such that for instance one of the two surfaces that are to be joined is a surface of the contraction device. The optical property of the contraction device is in particular its absorption degree for electromagnetic radiation with a predetermined spectrum, such that the absorption degree declines when the contraction device is heated above the predetermined temperature.

The temperature-dependent optical property of the solder or of the contraction device is in particular the absorption degree of the solder or of the contraction device for electromagnetic radiation with the predetermined spectrum, such that the absorption degree declines when the solder or the contraction device is heated above the predetermined temperature. In a medical or veterinary application the predetermined spectrum, in particular, lies in the near infrared range (about 780 nm or 750 nm up to 1.4 micro m), in which most tissues are not very absorbent.

The solder or the contraction device is radiated, for instance, with a predetermined intensity or a predetermined capacity within a predetermined time interval. The temperature of the solder rises in the predetermined time interval before the predetermined temperature is reached with a first segment and after the predetermined temperature is reached with a second segment that is smaller or essentially smaller than the first segment. For instance, the second segment can be one-half, one-third, one-fifth, or just one-tenth of the first segment or zero.

Before using one of the described methods, a type of tissue can be acquired on at least one of the two surfaces that are to be joined. A maximum temperature is ascertained, up to which any damage to tissue of the acquired type does not exceed a predetermined threshold. A solder or contraction device is selected and used in the method, such that the optical property of said solder or device alters at a temperature that is not greater than the ascertained maximum temperature. In the acquisition of the type of tissue, a distinction is made, for instance, between epithelial tissue (in particular, surface epithelial and glandular epithelial tissue) and supporting tissue (in particular, bone, cartilage, and fat tissue), muscle tissue, and nerve tissue. For the predetermined threshold for damage, use is made, for instance, of the boundary between a reversible and non-reversible damage. The corresponding maximum admissible temperature is taken, for instance, from a table. The predetermined temperature at which the temperature-dependent optical property of the solder or contraction device is modified lies, for instance, at 54° C. or below. It is possible to take into account that tissue damage depends not just on the temperature but also on the duration of the effect of the temperature and on the volume or mass of the affected tissue. In addition, one can consider that the solder or contraction device, at least in its interior, reaches a higher temperature than the bordering tissue.

With one of the described methods, an intensity or capacity of an electromagnetic radiation can be acquired that is transmitted, reflected, or dispersed by the solder or the contraction device. The radiation is ended, for instance, when the acquired intensity or capacity or an absolute or relative modification in the acquired intensity or capacity exceeds or falls below a predetermined threshold in at least one predetermined spectral range.

A solder for adhesive bond joining of two surfaces by moistening both surfaces with the molten solder and connecting the surfaces with the subsequently solidified solder has a reversibly or irreversibly temperature-dependent optical property, in particular a temperature-dependent absorption degree for electromagnetic radiation with a predetermined spectrum. The solder, in particular, comprises a polymer that is transparent for electromagnetic radiation with the predetermined spectrum and at least either a thermochromatic pigment or a thermochromatic dye. For instance, the solder comprises capsules with a sleeve that is transparent for electromagnetic radiation with the predetermined spectrum, and with thermochromatic pigment that is surrounded by the sleeve.

A contraction device comprises a reversibly or irreversibly temperature-dependent optical property, in particular a temperature-dependent absorption degree for electromagnetic radiation with a predetermined spectrum. The contraction device comprises in particular a polymer that is transparent for electromagnetic radiation with the predetermined spectrum and at least either a thermochromatic pigment or a thermochromatic dye. For example, the contraction device comprises capsules with a sleeve that is transparent for electromagnetic radiation with the predetermined spectrum, and with a thermochromatic pigment that is surrounded by the sleeve.

The solders described above, the contraction device s described above, and the solders and contraction device s used in the methods described above can comprise a temperature-dependent absorption degree for electromagnetic radiation with a predetermined spectrum in the infrared spectral range, which changes at a first predetermined temperature, and a temperature-dependent absorption, scattering, or fluorescent behavior in the visual range (approx. 380 nm to 750 nm or 780 nm), which changes at the first predetermined temperature or at a second predetermined temperature.

A control device for controlling an adhesive bond joining of two surfaces or for contracting a contraction device is configured for controlling one of the previously described methods. The control device can in particular comprise an input for acquiring a signal of a sensor for an electromagnetic radiation that is transmitted, reflected, or scattered by the solder or the contraction device.

A device for adhesive bond joining of two surfaces or for contracting a contraction device in or on a human or animal body includes the previously described control device and a light source for radiating the solder or the contraction device with electromagnetic radiation with the predetermined spectrum. In addition the device can include a sensor for acquiring electromagnetic radiation that is transmitted, reflected, or scattered by the solder or contraction device.

BRIEF DESCRIPTION OF THE DRAWINGS

Hereafter embodiments are described with reference to the appended illustrations:

FIG. 7 shows a schematic flow diagram of a method for adhesive bond joining of two surfaces.

FIG. 8 shows a schematic flow diagram of a method for shrinking a contraction device.

DETAILED DESCRIPTION OF THE INVENTION

Figure 1:
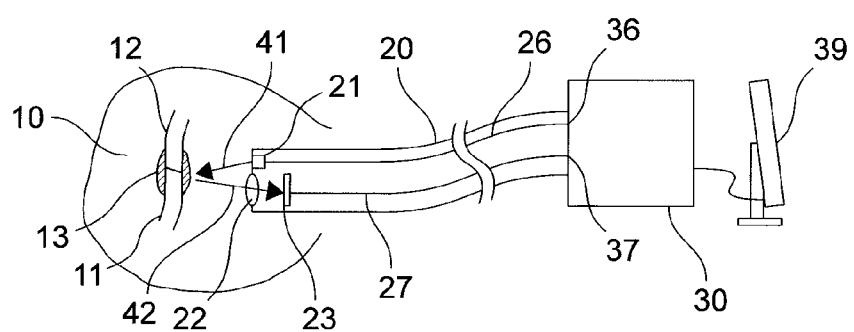
FIG. 1 shows a schematic depiction of a device for adhesive bond joining of two surfaces.

FIG. 1 shows a schematic depiction of a cross-section of a device for adhesive bond joining of two surfaces, in particular for adhesive bond joining of two surfaces in a human or animal body. In a hollow cavity 10 a first part 11 and a second part 12 are to be joined by means of a solder 13. The device includes an endoscope 20 whose distal end can be inserted in the hollow cavity 10. A light source 21, a lens 22, and an image sensor 23 are positioned on the distal end of the endoscope 20. The light source 21 is connected with an illumination line 26. The image sensor 23 is connected with an image line 27. The device further includes a control device 30 with an illumination output 36 that is coupled by the illumination line 26 with the light source 21 and an image signal input 37 that is coupled by the image line 27 with the image sensor 23. The device further includes a user interface 39, for instance a visual display unit and/or a keyboard or other input device, which is coupled with the control device 30.

The light source 21 is configured to emit heat radiation 41. For this purpose the light source 21 includes, for instance, an illumination diode or a semiconductor laser. The heat radiation includes, for instance, a predetermined spectrum in the near infrared range (wavelengths of approx. 780 nm or 750 nm to 1.4 micro m), in the mid-infrared range (1.4 micro m to 3 micro m), or in the far-infrared range (3 micro m to 1 mm). Because electromagnetic radiation in the near-infrared range is absorbed only to a minor degree by human or animal tissue, this spectral range is particularly appropriate.

The lens 22 is positioned, configured, and provided in order to focus scattered or reflected heat radiation 42 on the image sensor 23. The image sensor 23 can thus acquire an image of an object that is radiated with heat radiation 41 by the light source 21. In the example shown in FIG. 1, the image sensor 23 acquires an image of the first part 11, the second part 12, and the solder 13. The image acquired by the image sensor 23 is, for instance, depicted on the user interface 39 after preparation by the control device 30.

The light source 21 can be positioned on the proximal end of the endoscope 20 or in the control device 30 instead of on the distal end of the endoscope 20. In this case the light source 21 is coupled with the distal end of the endoscope 20 by a lightwave conductor. The image sensor 23 can be positioned on the proximal end of the endoscope 20 or in the control device 30 instead of on the distal end of the endoscope 20. In this case the image sensor 23 is coupled with the distal end of the endoscope 20 by an image line, in particular an oriented bundle of lightwave conductors. The proximal end of the endoscope 20, as shown in FIG. 1, can be coupled directly with the control device 30 or coupled with the control device 30 by a cable or a line.

Instead of the image sensor 23, a non-locally sensitive sensor can be provided for scattered or reflected heat radiation. The sensor or image sensor 23 can comprise, in addition to sensitivity for scattered or reflected heat radiation, also a sensitivity for electromagnetic radiation with other wavelengths. For example, the sensor or image sensor 23 is sensitive to wavelengths in the near-infrared range and in the visible range. The light source 21 can be configured to emit electromagnetic radiation with other wavelengths in addition to heat radiation 41. For example, the light source is configured to emit light in the near-infrared and in the visible ranges.

The device shown in FIG. 1 is configured to make possible an alignment of the distal end of the endoscope 20 on the interface between the first part 11 and the second part 12 and the solder 13, radiation of the solder 13 with the heat radiation 41 and an observation of the solder 13 by the image sensor 23. The soldering process that thus occurs is described in greater detail hereafter with reference to FIGS. 2 through 4.

Figure 2:
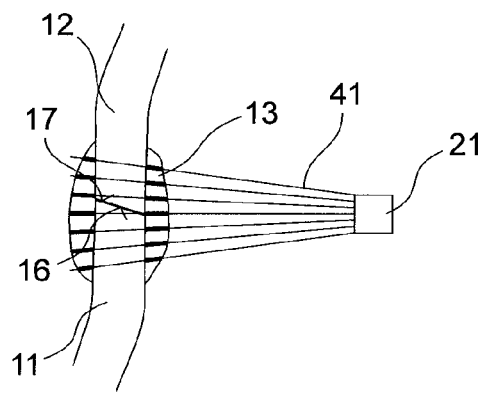
FIG. 2 shows a schematic depiction of two surfaces that are to be joined in an adhesive bond.

FIG. 2 shows a schematic depiction of a portion of FIG. 1 with additional details. It shows the first part 11, the second part 12, the solder 13, the light source 21, and the heat radiation 41 emitted by the light source 21. The first part 11 and the second part 12 are, for instance, ends of two blood vessels or ends of two tendons that are to be joined or mechanically connected with one another. In particular, a surface 16 of the first part 11 and a surface 17 of the second part 12 are intended to be connected with one another. The reference numbers 16 and 17 in FIG. 1 refer in particular to the mutually facing front surfaces of the first part 11 and of the second part 12. In fact, however, the mechanical connection occurs primarily by means of bordering sections of the covering surface of the first part 11 and of the second part 12, which are moistened by the solder 13 and mechanically joined after it has solidified. Therefore, the surfaces 16, 17 that are to be joined are hereafter intended to refer, in addition to the facing surfaces, also to the bordering covering surfaces of the first part 11 and the second part 12. In general the term "the surfaces that are to be joined" refers to the entire surfaces moistened with the solder.

In the depiction in FIG. 2, the solder 13 already moistens the surfaces of the parts 11, 12. This assumes as a rule that the solder 13 is already molten or has already melted.

The heat radiation 41 proceeding from the light source 21 is depicted in FIG. 2 without regard to its nature as an electromagnetic wave and as a number of photons, and without regard to its continuous intensity distribution by several individual straight beams. In addition, in the interest of simplicity, the refraction of the heat radiation on surfaces of the solder 13 and of parts 11, 12 is not shown. The beams that represent the heat radiation 41 are depicted there as thin lines where the heat radiation 41 is not absorbed or almost not absorbed, in particular in the hollow cavity filled with air, oxygen, or another fluid and in parts 11, 12. For this purpose, the wavelength of the heat radiation 41, for instance, is selected in such a way that it is not absorbed or almost not absorbed in parts 11, 12. In areas in which the heat radiation 41 is strongly absorbed, the beams representing heat radiation are depicted as broad lines. This is particularly true inside the solder 13. For this purpose the solder 13 is selected in such a way that it strongly absorbs the heat radiation 41.

The solder 13 includes, for instance as a matrix, a synthetic material that is essentially transparent for the heat radiation 41 with a melting point in a range between a few K above human or animal body temperature and 54° C. or a few K below it. It is advantageous here to use a synthetic material that is non-toxic for the human or animal body. Also advantageous is a synthetic material with degradability or reabsorption capability. The synthetic could be, for instance, polydiacetylene or a polymer derived from polydiacetylene. The solder 13, in addition, comprises a thermochromatic material (thermochromatic synthetic or thermochromatic pigment), which absorbs the heat radiation 41 when its temperature lies below or not above a predetermined temperature. The thermochromatic property can be an intrinsic property of the dye or pigment or can be derived from a reciprocal process of the dye or pigment with the polymer or with another component of the solder 13.

Because the heat radiation 41 is absorbed essentially only in the solder 13 or at least is more strongly absorbed by the solder 13 than by parts 11, 12, the light source 21 immediately exclusively or almost exclusively heats the solder 13 or at least heats the solder 13 more strongly or clearly more strongly than parts 11, 12 or other parts of the human or animal body. Indirectly, by heat conduction, convection, and heat radiation proceeding from the heated solder 13, parts 11, 12 and other parts of the human or animal body are heated, but as a rule do not reach the temperature of the solder 13.

The heat radiation 41 produced by the light source 21 can, as in FIG. 2, be divergent. The heat radiation 41 that impinges on the solder 13, however, can have a very low divergence or be focused on the solder 13 or partial areas of the solder 13, for instance in using a laser as a light source 21 and/or a collimator.

Figure 3:
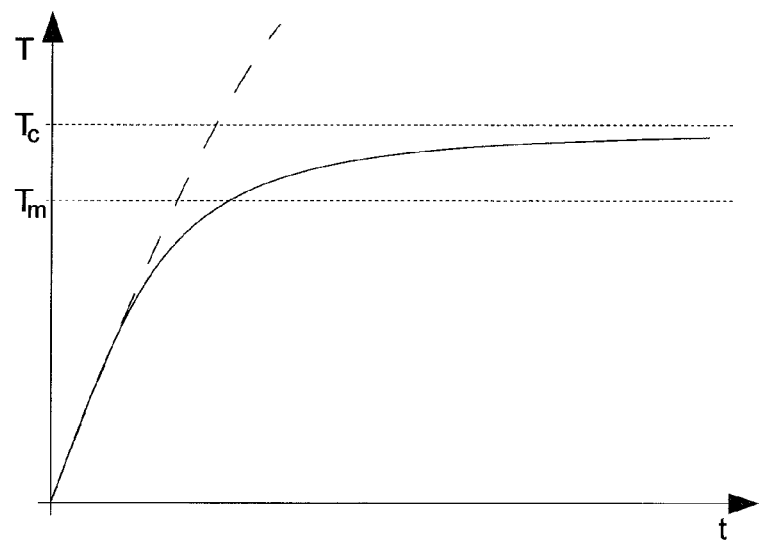
FIG. 3 shows a schematic diagram of a time-dependence of a temperature.

FIG. 3 shows a schematic diagram of the dependency of the temperature T of the solder 13 on time t. The abscissa indicates time t; the ordinates depict temperature T. The entry shows a minimal temperature $T_m$ that the solder 13 must reach in order to melt completely and to moisten the surfaces that are to be joined. The minimal temperature $T_m$, for instance, is indicated by the melting temperature of the solder 13 in addition to a safety margin. In addition, FIG. 3 shows a critical temperature $T_c$ that is not allowed to exceed the solder 13 in order to avoid thermal damage to bordering tissue (in particular of parts 11, 12).

In addition, a broken line in FIG. 3 indicates the course of the temperature in the case of a conventional, not thermochromatic absorption. The temperature of the solder at constant intensity of heat radiation 41 at first climbs in linear fashion. The speed of the rise is indicated by the intensity or capacity of the heat radiation 41, the absorption constant of the solder 13 for the heat radiation 41 and the heat capacity of the solder 13. With rising temperature, a slight flattening can be observed, which is caused by heat losses in the solder 13 at its periphery by heat conduction, convection, and heat radiation.

The time dependency of the temperature for a solder 13 with thermochromatic absorption behavior is indicated as an unbroken line. The absorption constant of the solder 13 for heat radiation 41 clearly declines at a predetermined temperature. For instance, the absorption constant within a temperature interval of 1K, 2K, 5K, or 10K decreases to one-half, one-third, one-fifth or one-tenth. An abrupt or non-continuous decrease is also possible, for instance caused by a phase transition of first order or similarly to a phase transition of first order.

The unbroken line in FIG. 3 shows a time dependency of temperature based on a decrease in the absorption of the heat radiation 41 by the solder 13 even below the minimal temperature $T_m$, where the absorption at temperatures between the minimal temperature $T_m$ and the critical temperature $T_c$ has already strongly declined. This absorption behavior can derive from a non-abrupt temperature dependency of the absorption behavior of the solder 13 and/or from the geometry of the volume filled by the solder 13.

The result is a time dependency of the temperature T of the solder 13 with a quick temperature rise for small temperatures, an already clear flattening of the temperature rise at the minimal temperature $T_m$, and a subsequent asymptotic proximity of the temperature T to a temperature below the critical temperature $T_c$. This temperature trend ensures that, assuming a sufficiently long radiation duration, the solder 13 will exceed the minimal temperature $T_m$ and thus will melt completely and will moisten the surfaces 16, 17 that are to be joined. Simultaneously this ensures that the temperature T of the solder 13 does not exceed the critical temperature $T_c$ even at extended radiation and that tissue bordering the solder 13 is not damaged or at least is not damaged above a predetermined extent.

Figure 4:
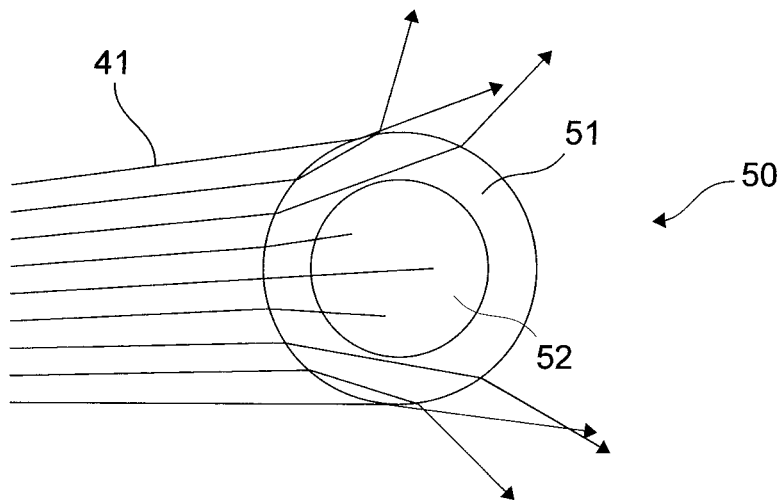
FIG. 4 shows a schematic depiction of a capsule with a thermochromatic pigment.

The solder 13, as mentioned, can comprise a thermochromatic dye or else thermochromatic pigment in a matrix that is transparent in itself for the heat radiation 41. A thermochromatic dye or thermochromatic pigment—for instance, a liquid crystal—can be dispersed in the matrix of the solder 13 in the form of microscopic capsules. FIG. 4 shows a schematic view of a cross-section through such a capsule 50 and heat radiation 41, which impinges on the capsule 50. The capsule 50 comprises a sleeve 51 that is transparent, or essentially transparent, for the heat radiation 41 and that surrounds the thermochromatic material 52. The fact that the thermochromatic material 52 is surrounded by a sleeve 51, for instance, is advantageous if the thermochromatic material has a toxic effect on the human or animal body or is not mixable with the matrix of the solder 13. The capsule comprises, for example, a diameter between 1 micro m and 100 micro m, in particular a diameter of 5 micro m. The entire space that is surrounded by the sleeve 51 contains, for instance, an undiluted dye or one that is diluted in an appropriate solution or embedded in a gel or other matrix, one or more particles of a pigment that are embedded in a solid matrix, or one or more particles of a pigment in a liquid. Alternatively, the sleeve 51 can surround, for instance, a single particle of a pigment.

FIG. 4 shows a sleeve 51 with a refractive index that is smaller than the refractive index of the matrix that surrounds the capsule 50. The result is a refraction of the heat radiation 41 on the outer surface of the sleeve 51, and on the border also a total reflection. This has two results. First, less heat radiation impinges on the thermochromatic substance 52; and second, the capsule 50 scatters the heat radiation 51 also at temperatures which are above the predetermined temperature and at which the thermochromatic substance 52 is transparent, or essentially transparent, for the heat radiation 41. The scattering extends the optic pathway of the heat radiation 41 in the solder 13 and thus increases its absorption. Therefore, in comparison with the use of a sleeve 51 as shown in FIG. 4 with a refractive index smaller than the refractive index of the surrounding matrix, it is better to use a sleeve 51 with a refractive index that is greater than the refractive index of the surrounding matrix. Especially advantageous is a sleeve 51 whose refractive index corresponds to the refractive index of the surrounding matrix. If the refractive index of the thermochromatic substance 52 surrounded by the sleeve 51 is freely adjustable, then it should be adjusted as precisely as possible to the refractive index of the sleeve 51 and the refractive index of the matrix surrounding the capsule 50, at least at temperatures above the predetermined temperature. The refractive index of the sleeve 51 or of the matrix is adjustable, for instance, by admixture of soluble, non-soluble, or difficult-to-dissolve sugars.

Figure 5:
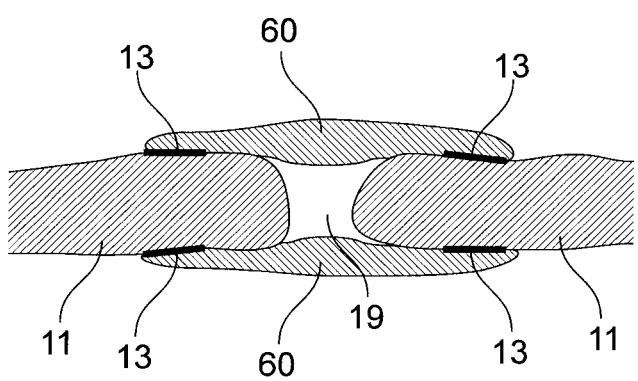
FIG. 5 shows a schematic depiction of a contraction device.
Figure 6:
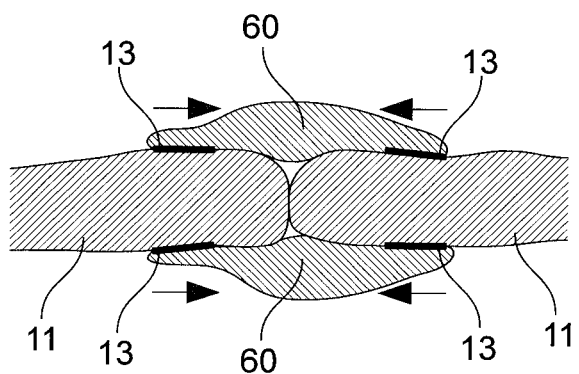
FIG. 6 shows a schematic depiction of the contraction device from FIG. 5 in contracted state.

FIGS. 5 and 6 show schematic views of a cross-section through a part 11 of a human or animal body and a contraction device 60. The part 11 is flat, and therefore in one dimension comprises a much smaller extension than in the two other dimensions. The part 11, for instance, is a wall of a stomach or of an intestine in a human or animal body. The cut surfaces shown in FIGS. 5 and 6 each lie perpendicular to the part 11 or to its local tangential plane.

The part 11 comprises a passage hole or orifice 19, as is produced for instance in the framework of NOTES (Natural Orifice Transluminal Endoscopic Surgery) in a stomach wall or intestinal wall and is closed up again at the conclusion of the procedure. The orifice 19 is closed by two contraction devices 60 positioned on opposite sides of the part 11. Each of the two contraction devices 60 is, for instance, plate-shaped or circular-shaped or elliptical or rectilinear and comprises an elastic, in particular biocompatible, material. Near its external border each contraction device 60 is joined or mechanically connected by solder 13 with the part 11. This occurs, for instance, in similar manner as indicated above with reference to FIGS. 1 through 4 in that the solder 13 is heated by heat radiation to a temperature above its melting point and thus is melted and after hardening forms an adhesive bond connection with the part 11 and the contraction device 60.

FIG. 5 shows the contraction devices 60 in an expanded position after their adhesive bond connection with the part 11. FIG. 6 shows the contraction devices 60 in a contracted state. After the adhesive bond connection with the part 11, the contraction devices 60 are converted from the expanded position shown in FIG. 5 to the contracted position shown in FIG. 6. The arrows in FIG. 6 indicate that in this process the lateral dimensions of the contraction devices 60 are reduced and the part 11 is contracted. In the process the aperture 19 is locked in the part 11 or at least clearly reduced in size. This allows a clearly accelerated healing of the orifice 19. The contraction devices 60 can comprise a material that can be broken down or reabsorbed by the human or animal body so that after healing of the orifice 19 the contraction devices 60 slowly disappear.

The lateral contraction of the contraction device 60 is based, for example, on a similar principle as in the contraction of shrink tubing used in electronics and electro-technology for electrical insulation, or as in the contraction of shrink wrap as is used for packaging of merchandise of all kinds or for covering wing panels in lightweight aeronautic construction and model construction. In particular, after the production and moistening of molecular chains of its material in contracted condition at an increased temperature, the contraction device 60 can be extended and then cooled in extended condition. In the process the extended condition is fixed or frozen. Upon repeated heating above a predetermined temperature, the contraction device then returns into the contracted position that it had assumed upon the moistening of the molecular chains of its material.

The lateral contraction of the contraction devices 60 can be triggered, for instance, thermally (in similar manner as with shrink tubing or shrink wrapping) or photochemically. For this purpose the contraction devices 60 comprise, for instance, the same dye or the same pigment as the solder 13 in order to absorb heat radiation. Alternatively the contraction devices 60 comprise, for instance, different dyes or pigments, which absorb at other wavelengths. As a result the soldering process and the shrinking or contraction process can be controlled independently of one another.

In any case, a thermochromatic property of the contraction devices 60 is advantageous, in particular the use of thermochromatic dyes or pigments in the contraction devices 60. As a result, similarly as described before with reference to FIGS. 1 to 4, the temperatures generated in the contraction devices 60 and in the bordering tissue can be restricted in order to prevent overheating and damaging of tissue.

Alternatively to a thermal shrinking of the contraction devices 60 caused by heat radiation, shrinking by means of other mechanisms is also possible. In addition, the contraction devices 60 can be joined with the part 11 by other means instead of by solder 13. For instance, the contraction devices 60 comprise an absorbent material that, because of its absorbability or the capillary action that is the basis of it, comes in contact with the surfaces of the part 11 and adheres to it.

Unlike the depictions in FIGS. 5 and 6, in addition both contraction devices 60 can be connected with one another by a strip of the same material and/or by a rod of another material. The strip and/or the rod can be used to position the contraction devices 60 on the orifice. Here a tube is first inserted into the orifice 19, for instance, by which the contraction units 60 connected with one another and folded by the strip and/or the rod are inserted into the orifice 19. The tube is then withdrawn in such a way that one of the two contraction devices 60 is unfolded on each side of the part 11 and, as shown in FIG. 6, comes in contact with the part 11. The rod can, depending on the situation, be released and removed from the orifice 19 before or after the shrinking or contraction of the contraction units 60, for instance by pulling backward, twisting, or screwing.

Instead of a point-like opening, one or two contraction devices can also close linear-shaped orifices in a part of a human or animal body. The depiction of a cross-section before and after the contraction of the contraction devices corresponds in this case to a considerable degree to the depictions in FIGS. 5 and 6.

FIGS. 7 and 8 show schematic flow diagrams of a method for adhesive bond joining of two surfaces or of a method for closing an orifice. Although both methods can also be used with apparatuses and devices as well as on bodily parts or workpieces that differ from those described above with reference to FIGS. 1 through 6, hereafter reference numbers from FIGS. 1 to 6 are used to facilitate clarity. The following methods described with reference to FIGS. 7 and 8 can be performed in combination with one another, in particular sequentially or partly simultaneously. In addition, both methods can be performed independently of one another. Some of the described steps are optional, as is mentioned below, partly explicitly once again.

FIG. 7 relates to a method for soldering or for adhesive bond joining of two surfaces by means of a solder. In a first step 101, a type of tissue is acquired on at least one of two surfaces that are to be joined in form-fitting manner. The type of tissue results, for instance, from the operational planning. In a second step 102, a maximum temperature is ascertained up to which any damage of tissue of the acquired type does not exceed a predetermined threshold. The second step 102 can occur by reference to a table. In a third step 103, a solder is selected whose absorption constant with reference to the range of a heat radiation foreseen for heating the solder decreases on exceeding a temperature that is lower or not greater than the ascertained maximum temperature. It is possible to dispense with the first step 101, the second step 102, and the third step 103 for instance, if only one solder is available that is appropriate for several or all tissues.

In a fourth step 104, the solder 13 is applied to at least one of the two surfaces to be joined in an adhesive bond. In a fifth step 105 the solder 13 is radiated with heat radiation 41. By absorption of the heat radiation 41, the solder 13 is heated to exceed its melting temperature and thus is melted. In a sixth step 106 the melted solder 13 moistens the surfaces 16, 17 that are to be joined. In a seventh step 107 the transparency of the solder 13 is increased. Alternatively, the degree of absorption is reduced or another optical property of the solder 13 can change. The seventh step 107 runs especially abruptly or continuously on reaching a predetermined temperature of the solder 13 or within a small temperature interval around this predetermined temperature.

In an optional eighth step 108, the intensity or capacity of an electromagnetic radiation transmitted or reflected or scattered by the solder 13 is acquired. If an absolute or relative modification of the acquired intensity or capacity exceeds or falls short of a predetermined threshold, the radiating of the solder 13 with heat radiation 41 is ended or the capacity or intensity of the heat radiation 41 is reduced.

In a ninth step 109, the radiating of the solder 13 with heat radiation 41 is ended. The ninth step 109 can be controlled after a predetermined time interval and/or, as already described, in some cases on the basis of the intensity or capacity acquired in the optional eighth step 108.

In a tenth step 110, the solder 13 cools after completion of the radiating process or earlier after reduction of its degree of absorption for the heat radiation 41, solidifies, and connects the surfaces 16, 17 that are to be joined in an adhesive bond.

FIG. 8 relates to a method for shrinking or contracting a contraction device 60. Before the steps described below, the steps corresponding to the previously described steps 101 to 103 with reference to FIG. 7 can be executed in order to select an appropriate contraction device.

In a first step 111, the contraction device 60 is applied to a surface of a part 11 of a human or animal body. This can be achieved with a method described above with reference to FIG. 7. Alternatively, however, the contraction device can also be cemented onto the part 11, or soldered or by other means connected with the part 11. For example, the part 11 can be connected to the part 11 by capillary forces or a capillary suction.

In a second step 112 the contraction device is radiated and heated by the capacity absorbed in that process. Because of the heating, the contraction device 60 shrinks or contracts. In the process, as discussed above with reference to FIGS. 5 and 6, an orifice 19, for instance, is closed. The contraction of the contraction device 60 occurs for instance starting at a first predetermined temperature or within a temperature interval. In a third step 113 the transparency is increased or the absorption constant of the contraction device is reduced for electromagnetic radiation with a predetermined spectrum. If the heating of the contraction device by electromagnetic radiation occurs with the predetermined spectrum, then a corresponding reduction of the absorbed capacity results from the reduced absorption constant. Consequently the temperature rise of the contraction device 60 is reduced or goes back to zero or the temperature of the contraction device 60 decreases.

In an optional fourth step 114, an intensity or a capacity of an electromagnetic radiation that is transmitted or reflected or scattered by the contraction device is acquired.

In a fifth step 115 the radiating of the contraction device 60 is ended or the intensity or capacity of the radiation is reduced. The fifth step can be time-controlled or controlled after completion of a predetermined time interval or in some cases in a dependency on the intensity or capacity acquired in the optional fourth step 114. In particular, the radiating of the contraction device 60 can be ended if the acquired intensity or capacity or an absolute or relative modification of the acquired intensity or capacity exceeds or falls below a predetermined threshold.

Both the solder 13 used in the embodiments described above with reference to FIGS. 1 through 7 and the contraction devices 60 of the examples described above with references to FIGS. 5, 6, and 8, in addition to a temperature-dependent absorption degree for electromagnetic radiation with a first predetermined spectrum (for instance in the near-infrared range), can comprise a temperature-dependent absorption, scattering, or fluorescent behavior in a second predetermined spectrum (for instance in the visible range). The temperature-dependent absorption degree for electromagnetic radiation with the first predetermined spectrum and the temperature-dependent absorption, scattering, or fluorescent behavior in a second predetermined spectral range can also be modified at the same predetermined temperature or at two different predetermined temperatures. The decrease in the absorption degree upon exceeding a first predetermined temperature results in an automatic or intrinsic or self-actuating regulation of the temperature of the solder 13 or of the contraction device 60. The modification of the absorption, scattering, or fluorescent behavior is appropriate for signaling the reaching of the second predetermined temperature by means visible to the human eye or by means that can be acquired with a corresponding sensor.

The invention is appropriate for joining a number of tissues, for instance for parenchymatous tissue (including kidney, liver, lung, spleen, brain, fatty tissue), collagen-containing tissue (including cartilage, blood vessels, ureters, tendons, lymph glands), bodily membranes (including skin, diaphragm, bladder, stomach wall, uterine wall, brain tissue, meningeal tissue, cornea, retina), myelin-containing tissue (including nerve vessels), muscle tissue, bones. Upon joining two vessels, the heat radiation can be conducted for instance by means of a lightwave conductor in one of the two vessels as far as the fusion site and distributed there, for instance by means of a reflecting sphere or diffuser in a ring-shaped space.

Beyond the previously described applications in human or veterinary medicine, the present invention is also appropriate for non-medical applications in various fields of technology. For instance, more uniform temperatures can be achieved with the present invention upon soldering synthetic materials and any local or large-scale overheating of the parts to be joined can be prevented.

What is claimed is:

1. A method for adhesive bond joining of two surfaces comprising the following steps:
    apply a metallic or non-metallic solder to at least one of the two surfaces, such that the solder has a temperature-dependent optical property for electromagnetic radiation with a predetermined spectrum in the infrared spectral range;
    radiate the solder with electromagnetic radiation with a predetermined spectrum in the infrared spectral range, such that the solder reaches a predetermined temperature above its melting temperature and moistens the surfaces by the molten solder, such that the temperature-dependent optical property is reversibly or irreversibly modified at the predetermined temperature of the solder, such that absorption constant of the solder decreases upon heating the solder;
    cool the solder below its melting temperature, such that the solder solidifies and connects the surfaces in adhesive bond manner.

2. The method according to claim 1, wherein at least one of the two surfaces is a surface of a part of a human or animal body.

3. The method according to claim 2, wherein the solder comprises a reversibly or irreversibly temperature-dependent optical property.

4. The method according to claim 1, in addition comprising the following steps:

apply a contraction device to at least one of the two surfaces;

radiate the contraction device with electromagnetic radiation with the predetermined spectrum or another predetermined spectrum, such that the contraction device reaches the predetermined temperature and contracts in at least one direction or changes geometrically in other manner, such that a temperature-dependent optical property of the contraction device is reversibly or irreversibly modified at the predetermined temperature of the contraction device.

5. The method according to claim 1, wherein the absorption constant of the solder for electromagnetic radiation with the predetermined spectrum clearly decreases upon heating of the solder above the predetermined temperature and thus the reception of electromagnetic radiation with a predetermined spectrum is clearly reduced.

6. The method according to claim 1, wherein
the solder is radiated within a predetermined time interval with a predetermined intensity,
the temperature of the solder in the predetermined time interval, before reaching the predetermined temperature, rises with a first segment and, after reaching the predetermined temperature, rises with a second segment that is smaller or essentially smaller than the first segment.

7. The method according to claim 1, in addition comprising the following steps:

acquire a type of tissue on at least one of the two surfaces;
ascertain a maximum temperature up to which any damage of tissue of the acquired type does not exceed a predetermined threshold;
select a solder whose optical property is modified at a temperature that is not greater than the ascertained maximum temperature.

8. The method according to claim 1, wherein the predetermined temperature is 54° C. or below.

9. The method according to claim 1, in addition comprising the following steps:
acquire an intensity or a capacity of an electromagnetic radiation that is transmitted or reflected or scattered by the solder;
end the radiating if the acquired intensity or capacity or an absolute or relative modification of the acquired intensity or capacity exceeds or falls below a predetermined threshold.

10. The method according to claim 1, wherein the solder comprises a polymer that is transparent for electromagnetic radiation with the predetermined spectrum and at least either thermochromatic pigments or a thermochromatic dye.

11. The method according to claim 1, wherein the solder comprises capsules with a sleeve that is transparent for electromagnetic radiation with the predetermined spectrum and that surrounds a thermochromatic pigment or a thermochromatic dye.

* * * * *